(12) United States Patent
Vermandel et al.

(10) Patent No.: US 8,666,133 B2
(45) Date of Patent: Mar. 4, 2014

(54) CALIBRATION PHANTOM AND METHOD FOR MEASURING AND CORRECTING GEOMETRIC DISTORTIONS IN MEDICAL IMAGES

(75) Inventors: Maximilien Vermandel, Loos (FR); Jean Rousseau, Loos (FR); Nacim Betrouni, Loos (FR); Pascal Briche, Lille Cedex (FR); Romain Viard, Loos Lez Lille (FR)

(73) Assignee: Institut National de la Santé et de la Recherche Médicale (INSERM), Paris (FR)

(*) Notice: Subject to any disclaimer, the term of this patent is extended or adjusted under 35 U.S.C. 154(b) by 145 days.

(21) Appl. No.: 13/395,997

(22) PCT Filed: Sep. 10, 2010

(86) PCT No.: PCT/EP2010/063329
§ 371 (c)(1),
(2), (4) Date: Apr. 20, 2012

(87) PCT Pub. No.: WO2011/029910
PCT Pub. Date: Mar. 17, 2011

(65) Prior Publication Data
US 2012/0201438 A1    Aug. 9, 2012

(30) Foreign Application Priority Data

Sep. 14, 2009  (EP) .................................. 09305842

(51) Int. Cl.
*G06K 9/00* (2006.01)
*G01D 18/00* (2006.01)
*A61B 5/00* (2006.01)

(52) U.S. Cl.
USPC ........................... 382/128; 378/207; 600/331

(58) Field of Classification Search
USPC ......... 382/123, 128, 129, 130, 131, 132, 133, 382/134, 275, 309; 378/207; 600/309, 331, 600/340, 410, 416, 449, 587; 128/920, 922
See application file for complete search history.

(56) References Cited

U.S. PATENT DOCUMENTS 6,005,916 A * 12/1999 Johnson et al. ................ 378/87
2004/0102691 A1 * 5/2004 Mallozzi et al. ............. 600/410

OTHER PUBLICATIONS

Ramani et al.; "A QA Phantom for Dynamic Stereotactic Radiosurgery: Quantitative Measurements"; Medical Physics, vol. 22, No. 8, Aug. 1, 1995; pp. 1343-1346.

(Continued)

*Primary Examiner* — Abolfazl Tabatabai
(74) *Attorney, Agent, or Firm* — Whitham Curtis Christofferson & Cook, PC

(57) ABSTRACT

Calibration phantom and method for measuring and correcting geometric distortions in an image of a body part of a patient Calibration phantom (5) for a medical imaging system, comprising a plurality of separate detection elements (20) arranged in a determined pattern, each detection element (20) containing a product that is visible by the medical imaging system.

8 Claims, 5 Drawing Sheets

(56) References Cited

OTHER PUBLICATIONS

Figure 1:
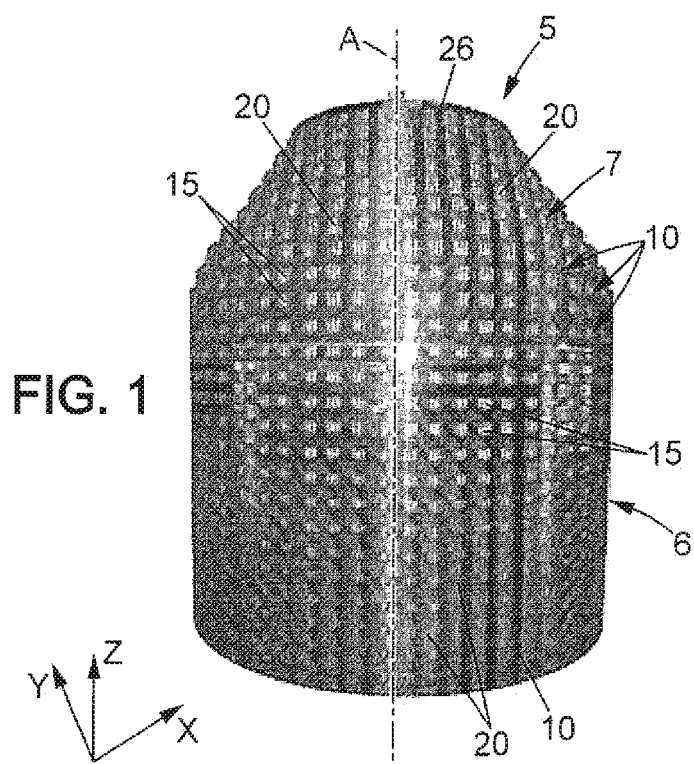

Mattila et al.; "Phantom-Based Evaluation of Geometric Distortions in Functional Magnetic Resonance and Diffusion Tensor Imaging"; Magnetic Resonance in Medicine, vol. 57, No. 4, Apr. 1, 2007; pp. 754-764.

Roamain Viard et al.; "Characterization and 3D Correction of Geometric Distortion in Low-Field Open-Magnet MRI"; 30th Annual Internationsl IEEE EMBS Conference, Aug. 20, 2008; pp. 3649-3652.

Wang et al.; "A Novel Phantom and Method for Comprehensive 3-Dimensional Measurement and Correction of Geometric Distortion in Magnetic Resonance Imaging"; Magnetic Resonance Imaging, vol. 22, No. 4, Jan. 1, 2004; pp. 529-542.

Fred L. Bookstein; "Principal Warps: Thin-Plate Splines and the Decomposition of Deformations"; IEEE Transactions on Pattern Analysis and Machine Intelligence, vol. 11, No. 6, Jun. 11, 1989; pp. 567-585.

* cited by examiner

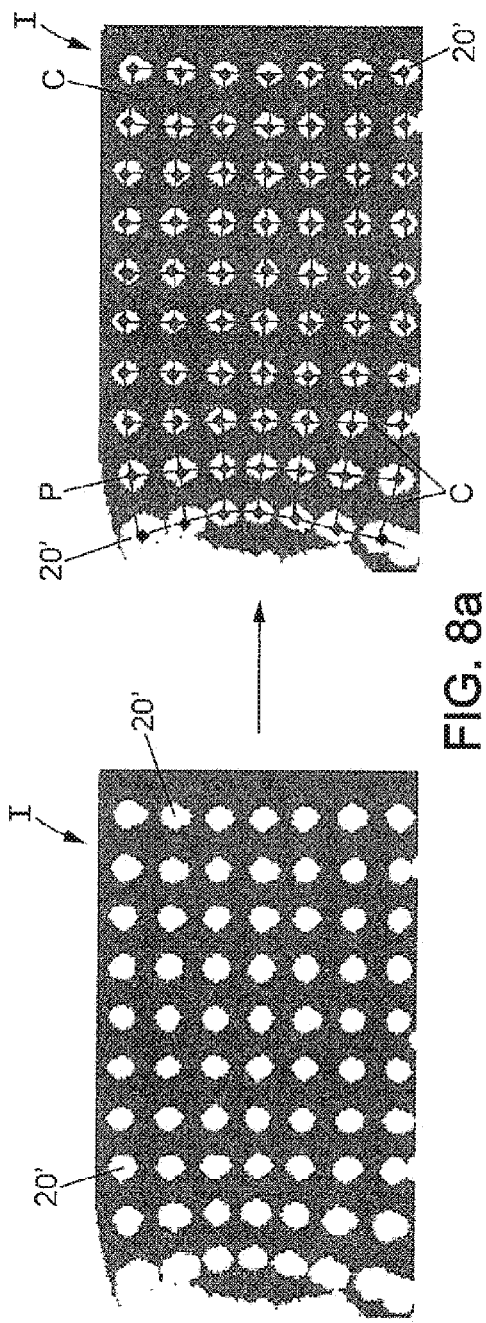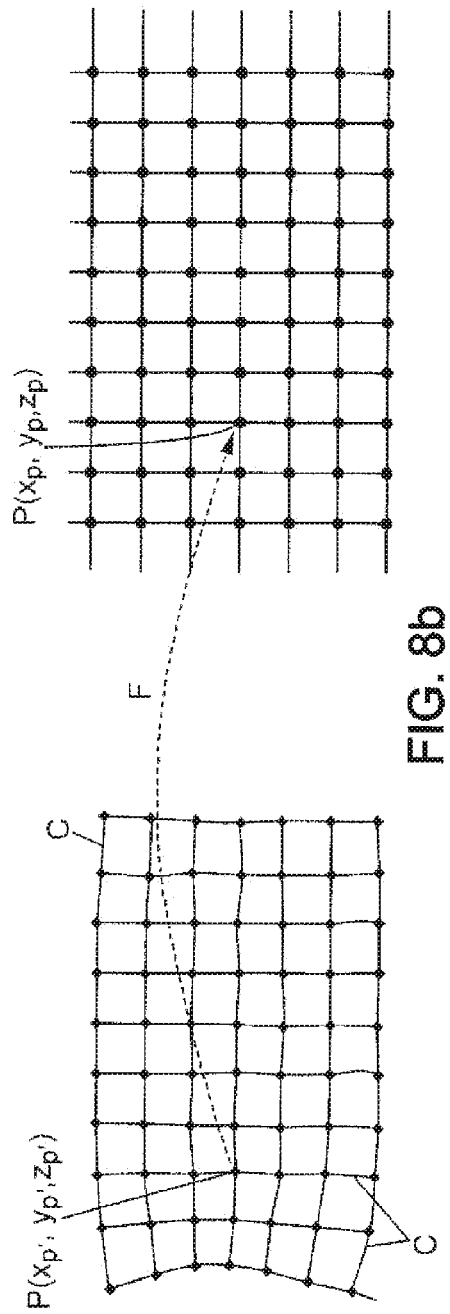
FIG. 8a
FIG. 8b

CALIBRATION PHANTOM AND METHOD FOR MEASURING AND CORRECTING GEOMETRIC DISTORTIONS IN MEDICAL IMAGES

The invention relates to a calibration phantom and to a method for measuring and correcting geometric distortions in an image of a body part of a patient.

In the medical field, an image of a body part obtained by a medical imaging system, such as a magnetic resonance imaging system, is known to be prone to geometric distortions. The image of the body part is therefore not necessarily an exact representation of the actual body part.

Sources of geometric distortions are various. For a magnetic resonance imaging system, among the possible sources, one can cite the geometric distortions induced by the imaging system itself, especially due to inhomogeneity of main magnetic field and nonlinearities of gradients, and the geometric distortions induced by the imaged body part, especially due to chemical shift and susceptibility variations within the imagined body part and at the air and tissue interfaces.

Images acquired for a purpose that requires an accurate spatial localisation, such as images for diagnosis or operation of the brain as well as abdomen, limb or others, need to be corrected as to such geometric distortions to reach the required accuracy.

A known method for measuring and correcting geometric distortions induced by the imaging system itself in an image obtained by the medical imaging system implements a calibration phantom that comprises a plurality of detection elements arranged in a determined pattern. To calibrate the imaging system, a correspondence between the positions of the detection elements on the image and their actual positions in the determined pattern is established.

A known calibration phantom implemented for calibrating a magnetic resonance imaging system comprises a plurality of spherical glass balls arranged in a support according to a three-dimension pattern. The balls and the support are invisible by the magnetic resonance imaging system. The pattern of glass balls is dipped into a bath of contrast agent visible by the magnetic resonance imaging system, such as copper sulphate ($CuSO_4$), so that the glass balls can be visualised on the image in hyposignal by contrast with the contrast agent that is visible in hypersignal ("Characterization and 3D correction of geometric distortion in low-field open-magnet MRI" by R. VIARD, N. BETROUNI, M. VERMANDEL, S. MORDON and J. ROUSSEAU, $30^{th}$ annual international IEEE EMBS conference, 20-24 August 2008, 3649-3652).

However, such known calibration phantom poses several problems. Actually, the known calibration phantom requires the balls to have a sufficient diameter. Furthermore, the balls need to be placed in an additional container filled with the contrast agent. The known calibration phantom is therefore of a large size and complex to carry out.

Besides, on the image of the known calibration phantom, both the balls and the support appear in hyposignal. Positions of the detection elements on the image are therefore difficult to detect.

Another known method for measuring and correcting geometric distortions with another known calibration phantom is disclosed in the article "A novel phantom and method for comprehensive 3-dimensional measurement and correction of geometric distortion in magnetic resonance imaging" by D. WANG, D. M. DODDRELL, G. COWIN, Magnetic Resonance Imaging 22 (2004), 529-542. However, this other known calibration phantom suffers from drawbacks analogous to that set forth above in terms of size, carrying out and detection difficulties.

Other calibration phantoms are known from US 2004/0102691 and from the articles "A QA phantom for dynamic stereotactic radiosurgery: quantitative measurements" by R. RAMANI, M. G. KETKO, P. F. O'BRIEN and M. L. SCHWARTZ, Medical physics 22 (August 1995), No. 8, 1343-1346, and "Phantom-based evaluation of geometric distortions in functional magnetic resonance and diffusion tensor imaging" by S. MATTILA, V. RENVALL, J. HILTUNEN, D. KIRVEN, R. SEPPONEN, R. HARI and A. TARKIAINEN, Magnetic resonance in medicine 57 (April 2007), No. 4, 754-763.

In addition to the above mentioned drawbacks, the known calibration phantoms provide for a resolution of the pattern that can hardly be varied.

The invention aims to solve the above mentioned problems.

To this end, according to a first aspect, the invention concerns a calibration phantom for a medical imaging system, comprising:

a plurality of separate detection elements arranged in a determined pattern, each detection element containing a product that is visible by the medical imaging system, each detection element comprising an envelop delimiting an internal volume filled with the product, and a support made of a material that is invisible by the medical imaging system so as to contrast with the product in an image of the medical imaging system, the support comprising a plurality of housings arranged according to the determined pattern, each housing being adapted to receive at least a part of one of the detection elements, the support comprising a plurality of plates provided with the housings, which housings are arranged along first and second directions, the plates being stacked along a third direction perpendicular to the first and second directions, wherein each plate presents opposed first and second surfaces, the respective first and second surfaces of two adjacent plates resting against each other, the envelop of each detection element has an external surface and each housing is adapted to receive entirely one of the detection elements so that a part of the external surface of said detection element is flush with the first surface of the plate.

Hence, since the detection elements are directly visible by the imaging system, the size of the detection elements can be reduced and the carrying out of the calibration phantom no longer requires any other step than an arrangement of the detection elements in the determined pattern. Range of possible sizes for the calibration phantom is thereby made larger, the calibration phantom being of small or large dimensions, depending on the use. The carrying out of the calibration phantom can be simplified.

Besides, the detection elements can be directly visible in hypersignal so that a subsequent processing of the image of the calibration phantom to detect the detection elements on the image and thereby to measure and correct the geometric distortions is made simpler and more accurate.

The material is invisible by the medical imaging system so that the detection of the detection elements is simplified.

The invention permits to ease the carrying out of the support and provide for an accurate positioning of the detection elements which are made in a simple manner.

Furthermore, the detection elements, and especially their centers of mass, can be spaced apart from each other of a known distance in the third direction corresponding to a thickness of the plates. The thickness of the plates may thereby define the resolution of the pattern. The resolution can be easily varied through a variation of the thickness of the plates.

To ease subsequent processing of the image of the calibration phantom, the detection elements may have a known simple shape. In particular, the detection elements may have the shape of balls, each detection element being spherical.

In one embodiment, the housings of each plate may consist in blind holes extending from the first surface of said plate.

To permit measurement and correction of geometric distortions in three orthogonal plans of the space, the determined pattern may be tridimensional, the detection elements being arranged in rows extending along three directions perpendicular to each other. At least one of the rows may comprise at least two reference detection elements of a dimension that is different from that of the other detection elements, so that at least one direction can be quickly identified and the orientation of the calibration phantom can be easily determined. Advantageously, the three directions are identified by reference detection elements.

According to a second aspect, the invention concerns a method for measuring and correcting geometric distortions in an image of a body part of a patient, comprising the following steps:
  providing a medical imaging system and a calibration phantom as previously defined,
  acquiring an image of the calibration phantom,
  measuring a field of geometric distortions on the basis of the calibration phantom and the image of said calibration phantom,
  acquiring an image of a body part of a patient,
  correcting the geometric distortions in the image of said body part through an application of the field of geometric distortions.

The method for measuring and correcting geometric distortions that is simplified and made more accurate thanks to the use of the calibration phantom of the invention provides for a robust processing of the images obtained by the imaging system.

In an embodiment, the step of measuring a field of geometric distortions may comprise the steps of:
  detecting a pattern of control points on the image of the calibration phantom, the control points deriving from an image of detection elements of the calibration phantom,
  matching each control point with one of the detection elements,
  calculating positional variations between each control point and the matching detection element in a reference frame of the medical imaging system.

In turn, the step of detecting a pattern of control points may comprise a step of calculating a center of mass of the image of each detection element of the calibration phantom.

Figure 2:
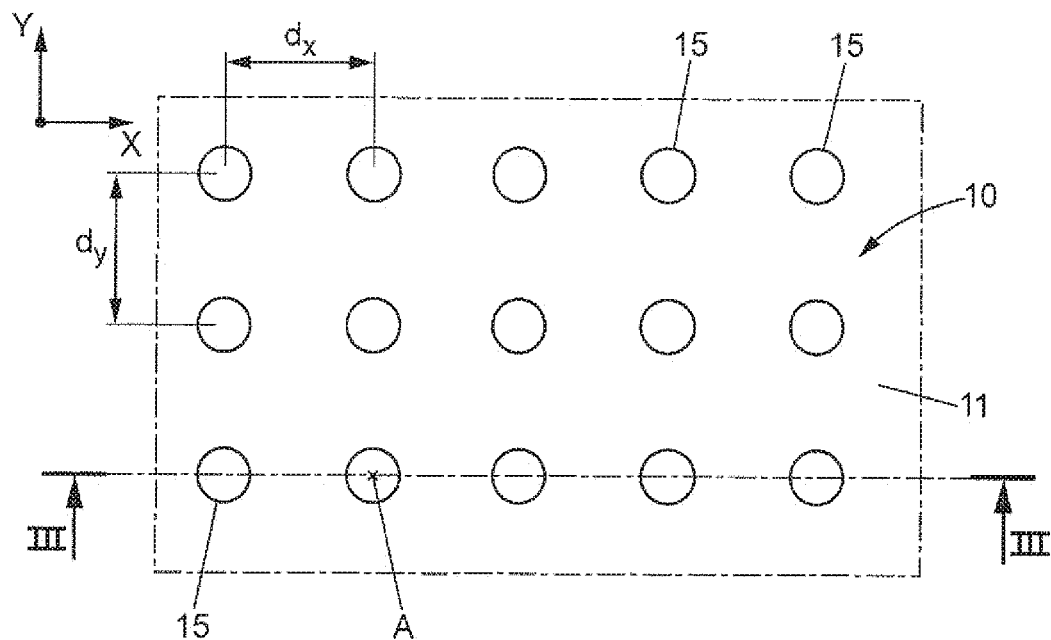
Figure 3:
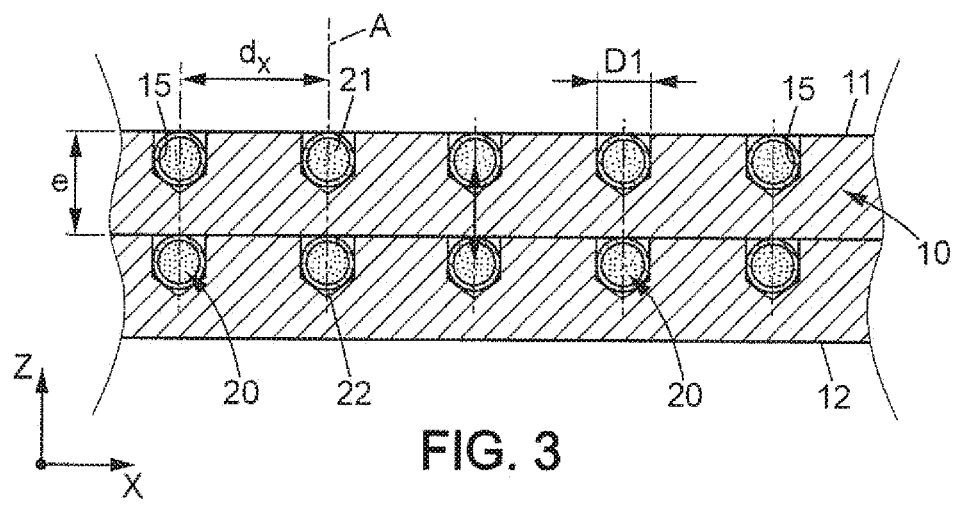
Figure 4:
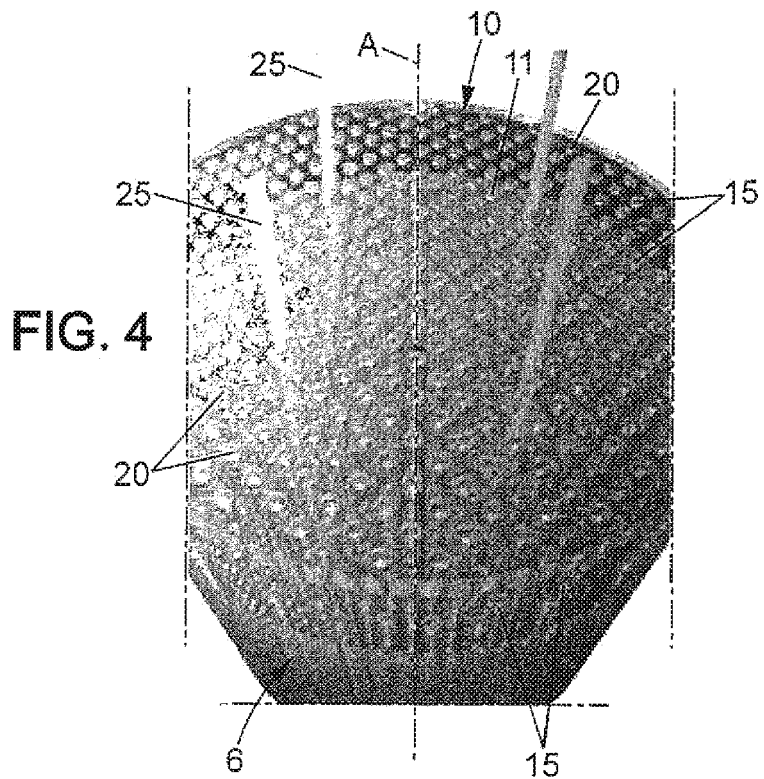
Figure 5:
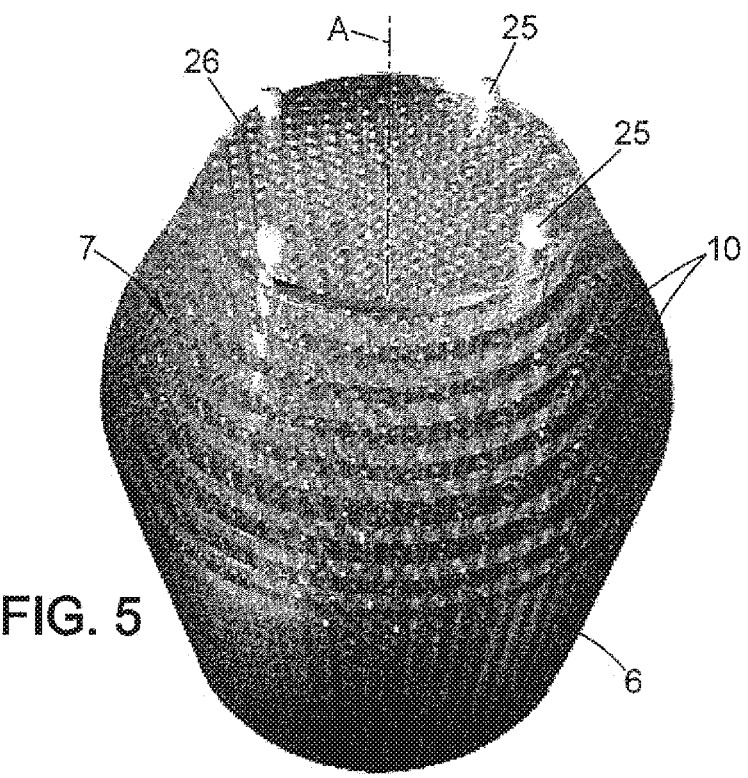
Figure 6:
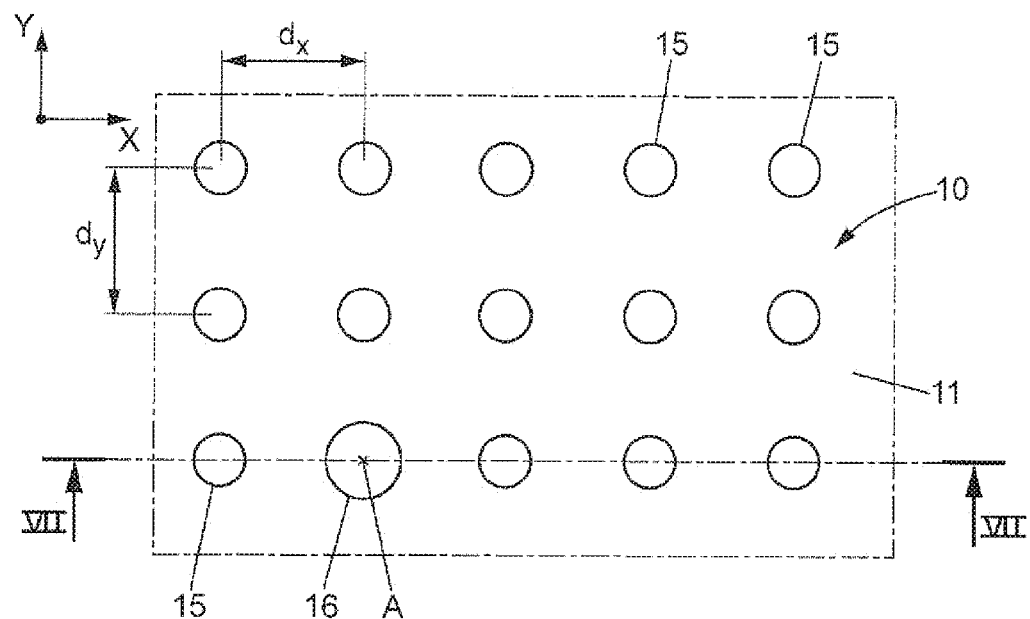
Figure 7:
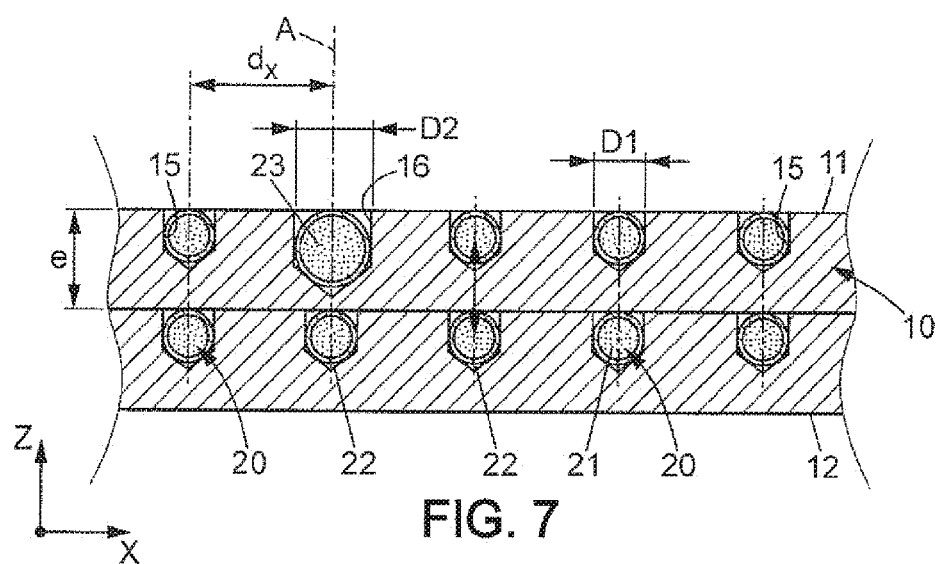

Other objects and advantages of the invention will emerge from the following disclosure made in reference to the enclosed drawings in which:

FIG. 1 is a perspective view of a calibration phantom for measuring and correcting geometric distortions in an image of an imaging system, the calibration phantom comprising a stack of plates provided with blind holes arranged in a three-dimension pattern, and detection elements housed in the blind holes, FIG. 2 is a top view of a part of the calibration phantom of FIG. 1, FIG. 3 is a sectional view along line referenced III-III on FIG. 2 of the calibration phantom of FIG. 1, FIGS. 4 and 5 are perspective views of an assembling process of the plates to form the calibration phantom of FIG. 1, FIGS. 6 and 7 are views similar to that of FIGS. 2 and 3 of a variant of the calibration phantom of FIG. 1, FIGS. 8a and 8b are schematic representations of steps of a method for measuring and correcting geometric distortions in an image acquired by an imaging system, the method implementing the calibration phantom of FIG. 1.

On the Figures, same references refer to similar or analogous elements.

FIG. 1 illustrates a calibration phantom 5 used for measuring and correcting geometric distortions in images acquired by a medical imaging system suitable for acquiring anatomical images, especially 2D or 3D images for diagnosis and/or operational purposes. The calibration phantom 5 is used, in particular, for calibrating the medical imaging system as it will be disclosed later in relation to FIGS. 8a and 8b.

In the illustrated embodiment, the calibration phantom 5 can be used to calibrate a magnetic resonance imaging (MRI) system as medical imaging system. For example, the illustrated calibration phantom 5 is designed and dimensioned to be placed within a head coil of the MRI system to measure and correct geometric distortions in an image of a head, a limb or any other body part of a patient for which such head coil is suitable.

For such application, the calibration phantom may have a base part 6 of cylindrical shape and a head part 7 of frusto-conical shape, arranged coaxially adjacent to one end of the base part 6.

In the represented embodiment, the calibration phantom 5 comprises a stack of plates 10 made of a material that is invisible by the medical imaging system, such as Plexiglas (Polymethyl Methacrylate, PMMA) or PVC in the case of the MRI system. On FIG. 1, the base part 6 comprises seventeen plates 10, referred to in the following as P1 for the plate opposite the head part 7 to P17 for the plate close to the head part 7, and the head part 7 comprises eight plates 10, referred to in the following as P18 for the plate close to the base part 6 to P25 for the plate opposite to the base part 6.

In particular, each plate 10 of the calibration phantom 5 extends generally perpendicular to a central axis A and presents a circular contour around the central axis A. The plates 10 of the base part 6 all have a same diameter whereas the plates 10 of the head part 7 have diameters that continuously decrease from the diameter of the plates 10 of the base part 6. As an illustrative example, the diameter of the plates P1 to P17 of the base part 6 is 230 mm. And the plates P18 to P25 of the head part 7 are respectively 224 mm, 214 mm, 200 mm, 182 mm, 170 mm, 156 mm, 144 mm and 130 mm in diameter.

Besides, each plate 10 of the calibration phantom 5 has a thickness e measured along the central axis A between opposed first 11 and second 12 surfaces. In the represented embodiment given as an illustrative example, the thickness e of the plates 10 is about 10 mm.

As can be seen on FIGS. 2 and 3, for each plate 10, the second surface 12 is full whereas the first surface 11 is pierced with an array of blind holes 15 parallel to the central axis A. In particular, the blind holes 15 of a diameter D1 are arranged in rows along a first direction X perpendicular to the central axis A and in rows along a second direction Y perpendicular to the central axis A and to the first direction X. In each row, the blind holes 15 may be regularly spaced apart from each other of a distance $d_X$, measured between centers of mass of two adjacent blind holes 15, in the first direction X and of a distance $d_Y$, measured between centers of mass of two adjacent blind holes 15, in the second direction Y. In the represented embodiment given as an illustrative example, the distances $d_x$ and $d_y$ are the same and measure about 10 mm.

Each plate 10 defines a support or a part thereof invisible by the MRI system and the blind holes 15 of each plate 10 define a regular two-dimension pattern of housings each adapted to receive a detection element 20 that can be directly visible by the MRI system.

The detection elements 20 represented on FIG. 3 are balls forming MRI capsules. Each detection element 20 comprises an envelop 22 bearing a spherical external surface and delimiting an internal volume filled with a product 21 that is visible by the MRI system. In a particular example, each detection element 20 is made of a soft-gelatine capsule type wherein the product 21 is propanediol which reduces chemical shift and the resulting geometric distortions.

The spherical shape of the detection elements 20 is given in a way of illustrative example. The detection elements 20 could be of any other shape defined by a closed external surface, the external surface delimiting an elementary volume of a determined geometry. Besides, depending on the medical imaging system, the product 21 of which the detection elements 20 are at least in part formed can be adapted so as to be visible by the medical imaging system. Examples of such products are water or copper sulphate ($CuSO_4$), an appropriate envelop being used where needed, such as for a product in a flowing form, to retain the product.

As can be seen on FIG. 3, the detection elements 20 are received respectively in the blind holes of each plate 10. For positioning reasons explained later, the blind holes 15 and the detection elements 20 are advantageously dimensioned so that each detection element 20 is received entirely in one of the blind holes 15 with a part of the external surface of the detection element 20 being flush with the first surface 11 of the plate 10.

In the represented embodiment given as an illustrative example, the diameter D1 of blind holes 15 may be 5.5 mm, the blind holes 15 having a depth of 5.5 mm, the detection elements 20 being 5.7 mm in diameter. The detection elements 20 of dimensions slightly bigger than that of the blind holes 15 can be frictionally retained within the blind holes 15.

In other embodiments, the support and the housings could be different from that disclosed previously so that only a part of the detection element 20 is received in the housing. For example, the plates 10 could be spaced apart from each other with blind holes 15 of convex shape for receiving a part of the external surface of the detection elements 20.

Besides, the description has been made with a material for the support that is invisible by the MRI system. Any material that provides for a contrast different from that of the product 21 of the detection elements 20 on the image obtained by the MRI system could however be used in accordance with the invention.

FIGS. 4 and 5 illustrate an assembling process of the plates 10 previously disclosed to form the calibration phantom 5 illustrated on FIG. 1.

In the represented embodiment, to ensure the securing and the orientation of the plates 10, each plate 10 may be provided with four through holes extending parallel to the central axis A. A fixing device comprises four rods 25 made of a material that is invisible by the MRI system, such as the same material as that of the plates 10.

Once the detection elements 20 have been placed in the respective blind holes 15 with a slight deformation of the detection elements 20 where needed, the through holes of the plates 10 are placed in correspondence with ends of the rods 25, and the plates 10 with their first surface 11 directed upwards are fitted on the rods 25 so as to be coaxially stacked along a third direction Z perpendicular to the first X and second Y directions, the respective first 11 and second 12 surfaces of two adjacent plates 10 resting against each other. In the stack, the plates 10 are so oriented that the through holes and the blind holes 15, and therefore the detection elements 20, are superposed in the third direction Z. As can be seen of FIG. 3, in the third direction, since the external surface of each detection element 20 is flush with the first surface 11 of the plate 10, the center of mass of two adjacent detection elements are spaced apart from each other of a distance that corresponds to the thickness e of the plates.

To maintain the stack of plates 10, the ends of the rods 25 may be attached in any suitable manner to end plates 26 made of a material that is invisible by the MRI system. In a variant, the plates 10 may be secured directly to the rods 25 by friction or through corresponding threads formed on the rods 25 and the through holes of the plates 10. In other embodiments, any suitable fixing device permitting to provide securing and orientation of the plates 10 in the above disclosed stack could be used. Besides, the fixing device could be made of a material that provides for a contrast different from that of the product of the detection elements on the image obtained by the MRI system.

Once the stack is formed, the calibration phantom 5 may be covered with a layer of varnish unvisible by the imaging system, to limit sensitivity to moisture.

The calibration phantom 5 therefore comprises rows of separate detecting elements 20 equally spaced along the first X, second Y and third Z directions perpendicular to each other. The calibration phantom 5 defines a regular three-dimension pattern of discrete elementary volumes formed of the detection elements 20 spaced apart from each other and arranged in a structure of a known geometry with a position that can be determined.

The distances $d_x$ and $d_y$ between the detection elements in the first X and second Y directions and the thickness e of the plates which corresponds to the distance between the detection elements in the third direction Z are chosen so that the calibration phantom 5 includes the appropriate number of detection elements 20. The distances $d_x$ and $d_y$ and the thickness e define a resolution of the three-dimension pattern according to which the correction of the geometric distortions will be made. Through an appropriate choice of the distances $d_x$ and $d_y$ and of the thickness e of the plates, the resolution of the three-dimension pattern can be adapted.

In the represented embodiment given as an illustrative example, the calibration phantom comprises eight thousand four hundred and seventeen (8417) detection elements 20 distributed as follow:

| Plate | Number of blind holes receiving one detection element |
|---|---|
| P1 to P17 | 385 in each plate 10 |
| P18 | 357 |
| P19 | 333 |
| P20 | 293 |
| P21 | 241 |
| P22 | 213 |
| P23 | 177 |
| P24 | 145 |
| P25 | 113 |

The above disclosed structure of the calibration phantom 5 allows for the implementation of a calibration phantom of relatively small dimensions, such as 230 mm large and 255.5 mm high in the illustrated embodiment, with a high resolution.

The shape and the dimensions of the represented calibration phantom 5 permit to cover a relatively small field of view (FOV) that is observed in the case of the application with the head coil of the MRI system.

Of course, the invention is not limited to the application to a head coil and could be applied for any other type of coil such as a body coil. The shape and the dimensions of the calibration phantom 5 could be adapted to any other application, especially through modifications of the shape and the dimensions of the support. The calibration phantom 5 could also be modified to cover a maximum FOV of the MRI system and to correct geometric distortions far from a magnetic center of the MRI system.

Besides, the calibration phantom 5 has been disclosed with a support formed of a stack of plates 10. The invention is however not limited to such support for the detection elements 20.

FIGS. 6 and 7 illustrate a variant of the calibration phantom 5 disclosed in relation to FIGS. 1 to 5. The variant of FIGS. 6 and 7 only differs from the calibration phantom previously disclosed in that it comprises reference blind holes 16 and reference detection elements 23 received within the reference blind holes 16 to orientate the calibration phantom. The description of the variant of FIGS. 6 and 7 will therefore not be resumed in detail.

In the variant, the calibration phantom is modified so that at least one of the rows in one of the first X, second Y and third Z directions, and advantageously one row in each of the first X, second Y and third Z directions, comprises at least two reference blind holes 16 with two reference detection elements 23.

As can be seen on FIG. 6, the reference blind hole 16 forms one of the housings of the array and has a diameter D2 larger than the diameter D1 of the other blind holes 15. The represented reference blind hole 16 extends along the central axis A of the plate 10. At least one other reference blind hole 16 (not shown) is aligned with the represented reference blind hole 16 along the first X, second Y and/or third Z directions.

FIG. 7 illustrates, through a sectional view along the line referenced VII-VII on FIG. 6, one of the reference detection elements 23 received in the reference blind hole 16. The represented reference detection element 23 has a diameter larger than that of the other detection elements 20 and presents a structure similar to that of the other detection elements 20. Besides, as for the other blind holes 15 of the array, the reference blind holes 16 and the reference detection elements 23 are dimensioned so that a part of the external surface of each reference blind hole 16 is flush with the first surface 11 of the plate 10.

In the represented embodiment given as an illustrative example, the diameter D2 of the reference blind holes 16 may be 6.75 mm, the reference blind holes 16 having a depth of 7.75 mm, the reference detection elements 23 being 7 mm in diameter. Twelve (12) reference detection elements are distributed in one reference blind hole 16 arranged in each of the plates P9 to P12 and P17 and seven reference blind holes 16 arranged in the plate P13.

As for the blind holes 15 previously disclosed, the support and the housings could be adapted so that only a part of the reference detection element 23 is received in the reference blind hole 16. For example, a counter blind hole facing the reference blind hole 16 of one of the plate 10 could be arranged in the second surface 12 of the adjacent plate 10 to receive the other part of the reference detection element 23. The reference blind holes 16 could have a depth of 6.75 mm whereas their diameter D2 remains 6.75 mm, the counter blind holes having a depth of 1 mm and a diameter of 6.75 mm.

The reference detection elements 23 arranged according to a trihedron the origin of which may be located at the centre of the calibration phantom define a reference frame of the calibration phantom. In the represented embodiment given as an illustrative example, three reference detection elements 23 define the first direction X, four reference detection elements 23 define the second direction Y and five reference detection elements 23 define the third direction Z.

It should be noted here that the reference detection elements 23 could be made in any other suitable manner so as to be distinguished with respect to the other detection elements 15. For example, reference detection elements 23 of smaller dimensions or of a different structure could be implemented.

In relation to FIGS. 8a and 8b, a method for obtaining an image of a body part of a patient corrected regarding geometric distortions is now disclosed.

A correction of the geometric distortions in the image is based on a three-dimension pattern of control points P obtained from the calibration phantom 5. From the pattern of control points P, a software may estimate geometric distortions thanks to the known geometry of the calibration phantom 5 and to the determined actual position of the detection elements 20.

Therefore, before the steps of acquiring the image of the body part of the patient and correcting the acquired image as to geometric distortions in a manner explained later, the MRI system is calibrated as illustrated on FIGS. 8a and 8b.

The calibration of the MRI system can be implemented at any suitable time, for example before the acquisition of an image with a new sequence. Furthermore, the calibration of the MRI system can advantageously be implemented periodically.

The calibration of the MRI system comprises the following steps:
  placing the above disclosed calibration phantom 5 within the head coil of the MRI system, the origin of the trihedron of the calibration phantom 5 being arranged approximately at the magnetic center of the MRI system,
  acquiring an image I of the calibration phantom 5,
  measuring a field F of geometric distortions on the basis of the calibration phantom 5 and the image I of the calibration phantom 5.

At least one image I of the calibration phantom 5 corresponding to the image to correct as regard to the geometric distortions is acquired. In a particular example, axial, sagittal and coronal images of the calibration phantom 5 at a regular interval are acquired through a determined sequence, such as an angiographic sequence. An example of an image I of the calibration phantom 5 wherein images of the detection elements 20' are visible in hypersignal is illustrated on the left part of FIG. 8a.

Once the images I of the calibration phantom 5 have been acquired, the field F of geometric distortions is measured by:
  detecting the pattern of control points P on the image I of the calibration phantom 5,
  matching each control point P with one of the detection element 20,
  calculating positional variations between each control point P and the matching detection element 20 in a reference frame of the MRI system the origin of which is at the magnetic center.

As shown on FIG. 8a, each image I of the calibration phantom 5 provides for an image of the detection elements 20'. Each control point P is determined on the basis of the image of one of detection elements 20' of the calibration phantom 5.

The images I of the calibration phantom 5 may be subjected to a low pass filtering, for example through a unitary 3*3*3 filter, before being subjected to a binarization. An example of a suitable automatic binarization is that of the method of OTSU disclosed in the article "A threshold selection method from gray-level histograms" by N. OTSU, IEEE, January 1979. A further filtration of the residual noise, for example through the method called Salt and pepper, may be implemented.

In a next step, a morphologic closing operation consisting in a dilatation combined to an erosion with a spherical structuring element of a dimension similar to that of the detection elements 20 may be used to regularise the shape of the image of detection elements 20'.

Each image I can then be segmented in groups of voxels and the position of each group of voxels is determined. To that end, a research of connected components and a filtering of the connected components as a function of their dimension and of that of the detection element 20 to be detected can be performed.

As shown on the right part of FIG. 8a, on the basis of the position of the groups of voxels belonging to the image of each detection element 20', a center of mass of the image of each detection element 20' may be calculated. In a particular embodiment, the position of each group of voxels may be weighted by the grey level of the groups of voxels in the native image. The calculated centers of mass the coordinates of which are known in the reference frame of the MRI system through the above disclosed treatment correspond to the control points P.

In an optional further step, the coordinates of the control points P can be recalculated by searching the intersection of curves C which link the centers of mass arranged in rows and columns. To that end, a polynomial approximation of order 3 may be performed.

The 3D coordinates in the reference frame of the MRI system having been calculated, the theoretical 3D coordinates of the centre of mass of each detection element 20 of the calibration phantom 5 the geometry of which is known can be calculated.

In order to quantify the geometric distortions, a match represented on FIG. 8b between each detected control point P and the actual center of mass of one of the detection elements 20 can be performed. For example, a centering is performed on the coordinates of the image of detection elements 20' and of the detection elements 20 by substantially superposing their center of mass. Then, an algorithm of rigid registration implementing three rotations and three translations and based on an optimisation of a distance criterion such as that of the closest points (Iterative Closest Points—ICP disclosed in the article "A method for registration of 3-D shapes" by P. J. BESL, N. D. McKAY, IEEE transactions on pattern analysis and matching intelligence 14 (2), 1992, 239-256) is used. Thereby, for each image of one of the detection element 20, the corresponding closest detection element 20 in the three-dimension pattern of the calibration phantom 25 is found.

The geometric distortions can be characterised by the differences between the measured 3D coordinates of each detected control point P and the actual position of the center of mass of the matching detection element 20 along the three directions of the reference frame of the MRI system 1:

$$dx_P = x_{P'} - x_P$$

$$dy_P = y_{P'} - y_P$$

$$dz_P = z_{P'} - z_P$$

$$dr_P = \sqrt{dx_P^2 + dy_P^2 + dz_P^2}$$

where $x_{P'}$, $y_{P'}$ and $z_{P'}$ are the coordinates of the control point P measured in the distorted image space and $x_P$, $y_P$ and $z_P$ are the corresponding theoretical coordinates of the control point P measured in the undistorted physical space of the calibration phantom.

To calculate the field of geometric distortion, i.e. the field F to apply to deform the detected control points P on the center of mass of the matching detection elements 20, an elastic or non rigid registration can then be performed, for example through the algorithm of thin-plate splines (SPM) as disclosed in the article "Principal warps: thin-plate splines and the decomposition of deformations" by F. BOOKSTEIN, IEEE transactions on pattern analysis and matching intelligence 11 (6), 1989, 567-585.

In a variant, the steps of matching each detected control point P with the actual center of mass of one of the detection elements 20 and of calculating the field of geometric distortion can be performed in a single step through the use of the algorithm of floating ICP as disclosed in the article "A new algorithm for non rigid point matching" by H. CHUI, A. RANGARAJAN, Computer vision and image understanding 89 (2-3), 2003, 114-141.

Finally, to correct the geometric distortions in the acquired image of the body part, the field F of geometric distortions is applied to each image acquired by the MRI system 1. The application of the field F of geometric distortions can be made through an interpolation to estimate the new intensities or grey levels of the images. Different methods can be implemented such as that of the radial basis functions (see article "Radial basis function interpolationon an infinite regular grid" by M. D. BUHMANN, M. J. D. POWELL, Algorithms for approximation II, J. C. MASON, M. G. COX, CHAPMANN and HALL, 1990, 146-169) and/or that of the cubic Hermine splines (see article "Cubic convolution interpolation for digital image processing. Acoustics, speech and signal processing" by R. KEYS, IEEE transactions on signal processing 29 (6), 1981, 1153-1160).

The method for measuring and correcting geometric distortions has been disclosed with respect to a correction in three dimensions. However, with the above disclosed methods could be applied with respect to a correction in two dimensions so that two-dimension coordinates are corrected.

Besides, the description has been made with the measurement and the correction of geometric distortions in an image obtained with a head coil of a MRI system. The invention could however be applied to medical imaging system of any other kind, the product contained in the detection elements and the material of the support being adapted accordingly.

As a way of example, for an imaging system employing tomography (CT), the product and the material would rather be of different contrasts. For example, the product of the detection elements could be distilled water providing for a low contrast, the material being of a density close to that of bone tissue, i.e. of a density close to 1.85 (z=13.8) corresponding to a Hounsfield density between 250 to 1000, and providing high contrast. For an imaging system employing positron emission tomography (PET), the product of the detection elements is a positron emitter, such as Germanium and other.

The invention claimed is:

1. Calibration phantom for a medical imaging system, comprising:
   a plurality of separate detection elements arranged in a determined pattern, each detection element containing a product that is visible by the medical imaging system, each detection element comprising an envelop delimiting an internal volume filled with the product, and
   a support made of a material that is invisible by the medical imaging system so as to contrast with the product in an image of the medical imaging system, the support comprising a plurality of housings arranged according to the determined pattern, each housing being adapted to receive at least a part of one of the detection elements, the support comprising a plurality of plates provided with the housings, which housings are arranged along first and second directions, the plates being stacked along a third direction perpendicular to the first and second directions, said calibration phantom being characterised in that each plate presents opposed first and second surfaces, the respective first and second surfaces of two adjacent plates resting against each other, the envelope of each detection element has an external surface and each housing is adapted to receive entirely one of the detection elements so that a part of the external surface of said detection element is flush with the first surface of the plate.

2. Calibration phantom according to claim 1, wherein each detection element is spherical.

3. Calibration phantom according to claim 1, wherein the housings of each plate consist in blind holes extending from the first surface of said plate.

4. Calibration phantom according to claim 1, wherein the determined pattern is tridimensional, the detection elements being arranged in rows extending along three directions perpendicular to each other.

5. Calibration phantom according to claim 4, wherein at least one of the rows comprises at least two reference detection elements of a dimension that is different from that of the other detection elements.

6. Method for measuring and correcting geometric distortions in an image of a body part of a patient, comprising the following steps:
   providing a medical imaging system and a calibration phantom according to claim 1,
   acquiring an image of the calibration phantom,
   measuring a field of geometric distortions on the basis of the calibration phantom and the image of said calibration phantom,
   acquiring an image of a body part of a patient,
   correcting the geometric distortions in the image of said body part through an application of the field of geometric distortions.

7. Method according to claim 6, wherein the step of measuring a field of geometric distortions comprises the steps of:
   detecting a pattern of control points on the image of the calibration phantom, the control points deriving from an image of detection elements of the calibration phantom,
   matching each control point with one of the detection elements,
   calculating positional variations between each control point and the matching detection element in a reference frame of the medical imaging system.

8. Method according to claim 7, wherein the step of detecting a pattern of control points comprises a step of calculating a center of mass of the image of each detection element of the calibration phantom.

* * * * *